United States Patent [19]

Zirino

[11] Patent Number: 5,334,629
[45] Date of Patent: Aug. 2, 1994

[54] CONTROL OF CONTINUOUS PHASE PH USING VISIBLE LIGHT TO ACTIVATE PH-DEPENDENT FIBERS AND GELS IN A CONTROLLED AND REVERSIBLE MANNER

[75] Inventor: Albert Zirino, San Diego, Calif.

[73] Assignee: The United States of America as represented by the Secretary of the Navy, Washington, D.C.

[21] Appl. No.: 936,681

[22] Filed: Aug. 27, 1992

[51] Int. Cl.$^5$ ............................................. G21K 1/10
[52] U.S. Cl. .................... 523/137; 252/500; 252/510; 60/527; 60/530; 524/503; 524/513; 524/514
[58] Field of Search ................. 60/527, 530; 523/137; 252/500, 510; 524/503, 514, 513

[56] References Cited

U.S. PATENT DOCUMENTS

| | | | |
|---|---|---|---|
| 3,646,615 | 3/1972 | Ness | 623/14 |
| 3,882,551 | 5/1975 | Helmer et al. | 623/14 |
| 4,358,355 | 11/1982 | Kalu et al. | 522/116 |
| 4,732,930 | 3/1988 | Tanaka et al. | 524/742 |

OTHER PUBLICATIONS

A. J. Campillo et al, "The Laser pH Jump" *International Conference on Lasers '78*, Orlando, Fla., Dec. 11-15, 1978, pp. 232-239.

T. Tanaka et al, "Phase Transitions in Ionic Gels", *The American Physical Society*, vol. 45, No. 20, Nov. 17, 1980, pp. 1636-1639.

T. Tanaka et al, "Critical Behavior of Density Fluctuations in Gels", *Physical Review Letters*, vol. 38, No. 14, Apr. 4, 1977, pp. 771-774.

T. Tanaka, "Collapse of Gels and the Critical Endpoint", *The American Physical Society*, vol. 40, No. 12, Mar. 20, 1978, pp. 820-823.

A. J. Campillo et al, "Excited-State Protonation Kinetics of Coumarin 102", *Chemical Physical Letters*, vol. 67, No. 2,3, Nov. 15, 1979, pp. 218-222.

J. H. Clark et al, "Picosecond Studies of Excited-State Protonation & Deprotonation Kinetics, The Laser pH Jump", *American Chemical Society*, 1979, pp. 746-748.

A. Suzuki et al, "Phase Transition in Polymer Gels Induced by Visible Light", *Letters to Nature*, vol. 346, Jul. 26, 1990, pp. 345-347.

A. Mamada, "Photoinduced Phase Transition of Gels", *American Chemical Society—Macromolecules*, 1990, 23, 1517-1519.

M. Irie et al, "Photoresponsive Polymers. 8. Reversible Photostimulated Dilation of Polyacrylamide Gels Having Triphenylmethane Leuco Derivatives", *American Chemical Society—Macromolecules*, 1986, 19, 2476-2480.

*Primary Examiner*—Paul R. Michl
*Assistant Examiner*—John J. Guarriello
*Attorney, Agent, or Firm*—Harvey Fendelman; Thomas Glenn Keough

[57] ABSTRACT

A transparent polyelectrolyte fiber or gel, such as crosslinked polyacrylic acid, which contracts and expands upon the addition of an acid or base to an aqueous medium solution, is placed in the same solution with a pH dependent dye, a colored photochromatic indicator dye. The dye preferably has a $pA_a$ value that is the same as the pH at a null contraction point of the fiber. By irradiating the solution with light of a wavelength of the absorption band of either the acid or base form of the dye, the solution pH is made to change, and the fiber is made to expand or contract, depending upon the wavelength. Thus, light energy is readily converted to work energy and may be used to power a pump, for example, or an artificial muscle can be powered via an optical fiber.

60 Claims, 2 Drawing Sheets

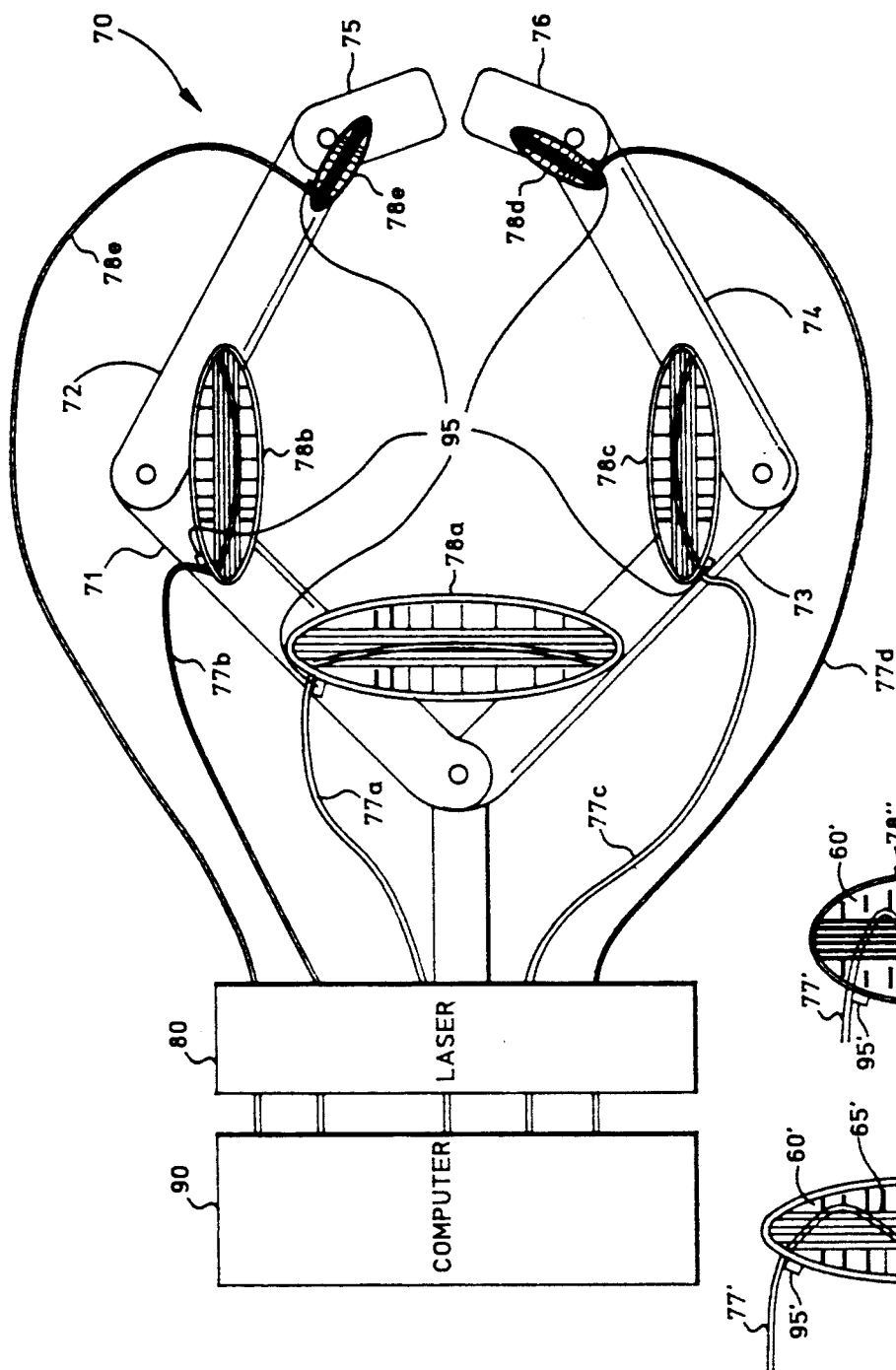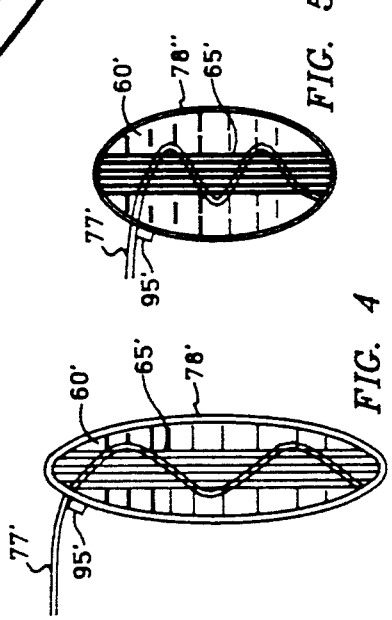

CONTROL OF CONTINUOUS PHASE PH USING VISIBLE LIGHT TO ACTIVATE PH-DEPENDENT FIBERS AND GELS IN A CONTROLLED AND REVERSIBLE MANNER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Synthetic (plastic) fibers which contract and expand upon stimulation with acid, heat, electrical current and light have been known for some time, see the article by Y. Osada, entitled "Conversion of Chemical into Mechanical Energy by Synthetic Polymers," *Adv. in Polym. Sci* 82, Springer Verlag, Berlin, Heidelberg, 1987. However, a good mimic of the human or animal muscle by a natural or synthetic fiber has been difficult to say the least since there has been no way to distribute the muscle-activating energy quickly to the fibers to enable responsive motion.

Thus, a continuing need exists in the state of the art for a means of supplying activating energy to natural or synthetic fibers, such as polyelectrolyte fibers or gels, which respond to pH changes in a pH dependent solution by changing their volume, thereby enabling the fibers to do work in response to selected wavelengths of impinging electromagnetic radiation.

SUMMARY OF THE INVENTION

The present invention is directed to providing an apparatus for and method of radiation-actuation of a polyelectrolyte fiber or gel. A pH dependent dye solution is responsive to discrete incident radiation to change its pH. A polyelectrolyte fiber or gel disposed in the pH dependent dye solution has the property to change its volume in response to pH changes in the pH dependent dye solution. A source of the discrete incident electromagnetic radiation is oriented to direct the discrete incident electromagnetic radiation on the pH dependent dye solution and polyelectrolyte fiber or gel to effect a change in pH in the pH dependent dye solution and a consequent change in volume in the polyelectrolyte gel.

An object of the invention is to provide an apparatus for and a method of selective electromagnetic radiation actuation of a polyelectrolyte fiber or gel.

An object is to provide an apparatus for and a method of selective electromagnetic radiation actuation of a polyelectrolyte fiber or gel that minimizes heat production.

Another object is to provide an apparatus for and a method of selective actuation of a polyelectrolyte fiber or gel by discrete wavelengths of electromagnetic radiation to cause a responsive expansion and/or contraction thereof.

Yet another object is to provide an apparatus for and a method of a responsive polyelectrolyte fiber actuation that changes the pH of a pH dependent dye solution by select wavelengths of electromagnetic radiation.

Another object is to provide an apparatus for and a method of fiber actuation by select wavelengths of electromagnetic radiation that changes the pH of a pH dependent dye solution to responsibly and reversibly contract or expand substantially all of an immersed polyelectrolyte fiber simultaneously.

Another object of the invention is to provide an apparatus for and a method of the selective expansion and contraction of a polyelectrolyte fiber by impinging select wavelengths of electromagnetic radiation that avoids the need for adding acid or base solutions.

Another object is to provide an apparatus for and a method of a substantially delay-free actuation of a natural or synthetic polyelectrolyte fiber by impinging select wavelengths of electromagnetic radiation to avoid the need for a diffusion of hydrogen or hydroxide ions in individual fiber sites.

Another object is to provide actuators of both great strength and tactile sensitivity to enable the fabrication of working robots or prosthetic devices.

These and other objects of the invention will become more readily apparent from the ensuing specification and claims when taken in conjunction with the appended drawings.

BRIEF DESCRIPTION OF THE DRAWINGS

FIG. 3 shows muscle pods actuated by optical fibers to articulate a claw-like device.

FIGS. 4 and 5 show extended and contracted muscle pods.

DESCRIPTION OF THE PREFERRED EMBODIMENT

Figure 1:
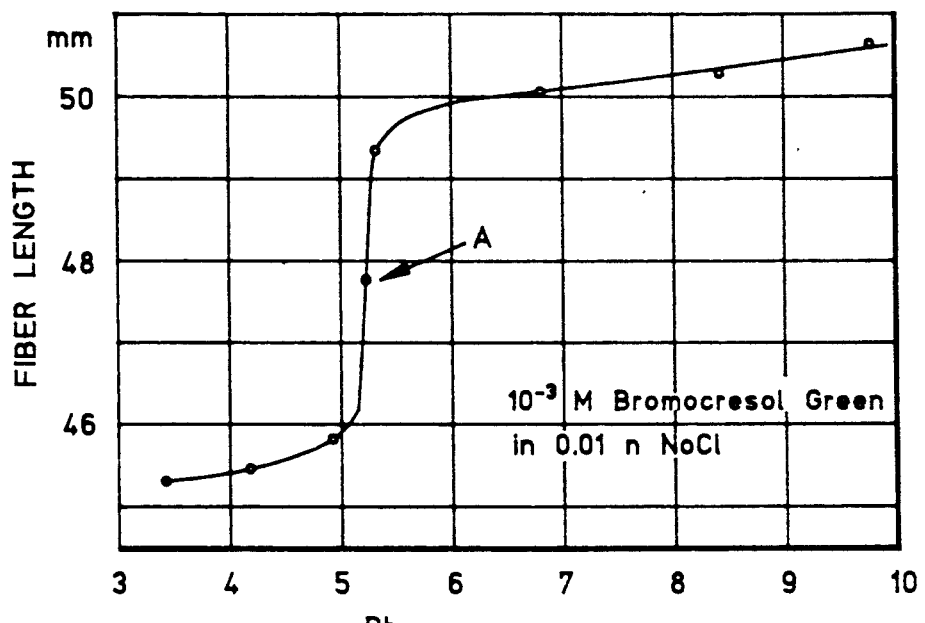
FIG. 1 is a graphical representation of the interrelationship associated with a change of fiber length of a polyelectrolyte fiber, such as a polyvinyl alcohol-polyacrylic acid (PVA-PAA) fiber, in a pH dependent dye solution, such as a $10^{-3}M$ Bromocresol Green solution, at the null point of the fiber at pH=5.3 of the solution; blue light at 450 nm makes the solution more basic and yellow light at 600 nm makes the solution more acidic to assure selective changing of the length of the fiber by changing the wavelength of the impinging light.

Referring now to the graph of FIG. 1 of the drawings, a polyelectrolyte fiber, or when hydrated, polyelectrolyte gel, such as cross-linked poly-acrylic acid (PAA-PAA), when placed in an aqueous solution or saline solution containing a pH-dependent dye, such as Bromocresol Green, responsively deflects, or changes volume, as select wavelengths of electromagnetic radiation, such as light, visible light, such as (yellow and/or green) impinge upon it. The polyelectrolyte fiber inherently has the property of changing its length or volume in response to changes of the pH of the solution in which it is immersed. The pH dependent dye solution inherently has the property of changing its pH in response to select wavelengths of impinging electromagnetic radiation. By immersing the polyelectrolyte fiber in the solution made up of a suitable pH dependent dye which changes its pH in response to impinging light and radiating it with impinging electromagnetic radiation of select wavelengths, responsive actuation of the fiber results.

A condition for the fiber that is termed as a null point A appears on the steep portion of its response curve. This null point A occurs at about a pH of 5.3 for this particular polyelectrolyte fiber. When the pH of a particular pH dependent dye solution varies either way from pH=5.3 in a range, for example, of plus or minus one pH unit, then the length or volume of the particular fiber in the particular solution changes in a rather pronounced manner as compared to the effects produced by somewhat greater pH changes outside of the plus and minus one pH range. It is apparent that the pH of the solution be maintained at a value that is substantially equivalent to the null point of the polyelectrolyte fiber for more acceptable operational results and can be expressed that the acid dissociation constant pKa be within a range that is within plus or minus 1 pH unit of the pH null point of the polyelectrolyte fiber or gel, (pH−1<pKa<pH+1).

Another property of a particular pH-dependent dye which is selected for use in accordance with this inventive concept is that the pH-dependent dye changes color on either side of the null point pH value. Bromocresol Green, for instance, is yellow at pH 2 and is blue-green at pH 6.6. By shining an intense yellow light on a pH 6 Bromocresol Green solution, the solution can be made more acidic, thus causing a suitable polyelectrolytic gel or fiber, such as polyvinyl alcohol-polyacrylic acid (PVA-PAA) to appropriately contract. Terminating the radiance causes the fiber to extend to its original dimension. Under acid conditions illumination of the solution containing the fiber with a blue light would shift the pH to a lower value to effect an extension of the fiber. The closer the null point of a fiber matches the pKa of the pH dependent dye, or indicator, the more work that may be done for a certain quality of light. The term pKa is the negative logarithm of the acid dissociation constant and is represented by $$K_{diss}=[H^+][A^-]/[HA]$$

where $H^+$ is the hydrogen ion concentration and $A^-$ is the concentration of the conjugate base. The pH change of the selected solutions is reversible, so that the pH returns to its former state as the light is turned OFF. Therefore, it is not always necessary to switch filters, i.e. radiate a different wavelength of light to change the pH to bring a fiber to its original condition. The use of filters may be preferred when the pH of the solution is at the null point pKa of the fiber to take advantage of the more extreme fiber excursions possible in this region as mentioned above.

Activation with a single wavelength may be achieved, for example, if the pH of the saline solution is lightly buffered with common chemical buffering agents to be slightly either to the left or right of the null point of the chosen fiber. Typical chemical buffering agents that may be selected are acidic acid/acetate, phosphoric acid/phosphate and boric acid/borate. With these agents, the pH of the saline solution around the fiber may be set to any pH value between 4 and 10.

After the buffering agent has been added to the saline solution, the pH-dependent dye is added. The appropriate dye is chosen to have a good absorption band in the selected pH region. The buffered-pH solution is irradiated with the right electromagnetic wavelength. The fiber responsibly changes volume (contracts or expands), as the case may be.

At the end of this part of the cycle (contraction or expansion), a light barrier may be placed in the optical path between a light source and the solution to allow the fiber to return to its former state. Clearly, as it returns to its previous length, the activation light may be reintroduced in the manner described herein. A spring might be added to aid in the restoration of the system.

Addition of chemical buffering agents assures that the pH of the solution can be custom-adjusted to suit the chosen fiber. In addition, a particular pH-indicator dye needs to have only one absorption band, e.g., a wavelength absorption band on the "driving" side of the fiber; the other side of a rotatable bracket, to be described below, can be opaque. As a consequence, the system may be inherently simpler.

In view of the foregoing, it is well within the purview of the routineer to fabricate a solar operated pump for desalination by reverse osmosis. The "muscle" can be made to contract and expand autonomously using solar energy, thereby driving a pump for a reverse osmosis system. The beauty of such a system is that few mechanical parts are required. For instance, the muscle can be made to contract with yellow light and expand with blue light or to relax with no light. The reaction will be in a sufficient time frame to be effective. A plate, evenly divided in yellow and blue windows is placed between sunlight and the muscle. As the muscle contracts with the yellow light it pushes water through a one-way valve. The motion of the muscle also rotates the disc. At point of maximum contraction, the yellow window is replaced by the blue window, which now causes the muscle to expand. Water is now taken in, again through a one-way valve, until maximum expansion, at which point the filter is switched again, and the muscle begins to contract. The system that seems most suited would be PVA-PAA fiber which has a pH of approximately 5.3 with tetrabromo-m-cresol sulfonphthalein which has a pKa of 4.90.

Figure 2:
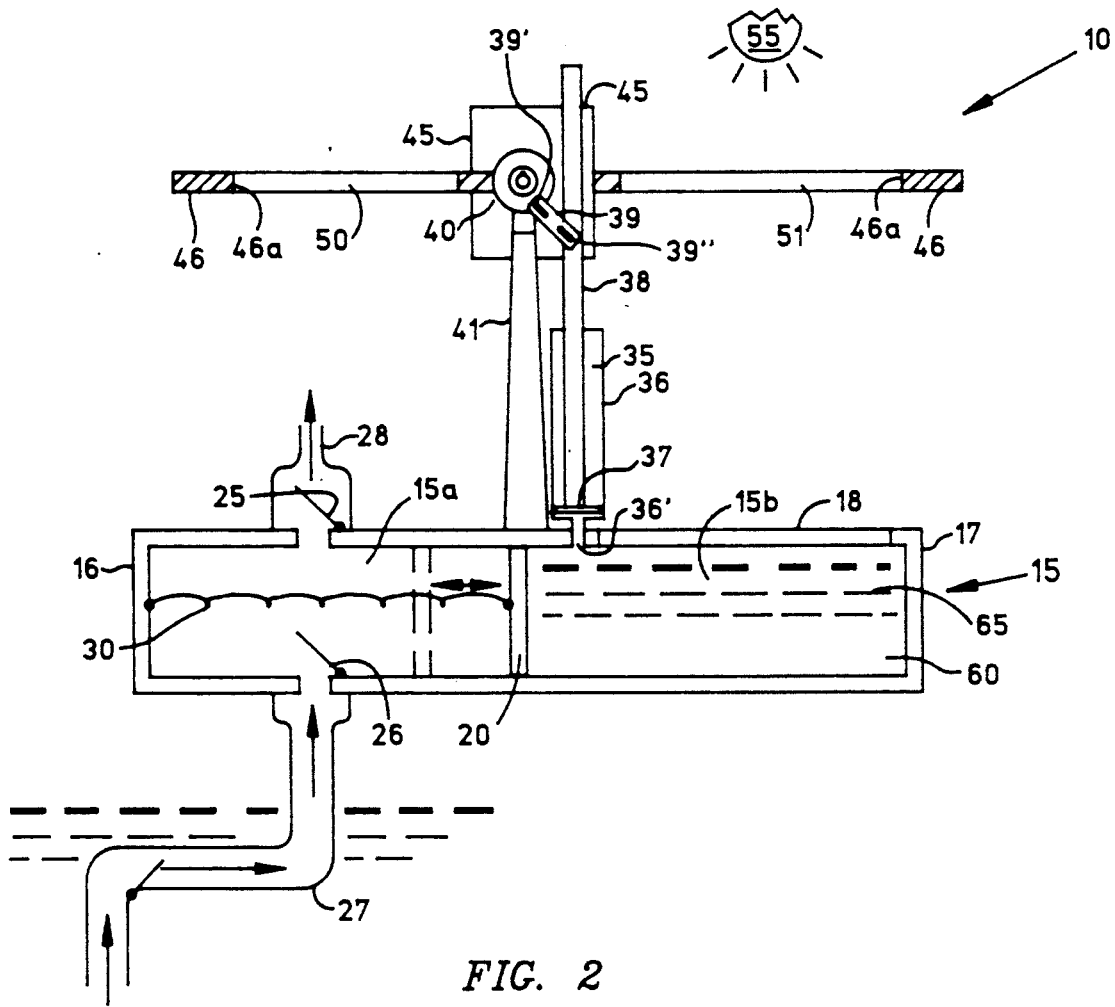
FIG. 2 represents an application of a light-powered fiber or gel muscle to provide a solar powered pump that is useful for the conversion of fresh water from seawater.

Referring now to FIG. 2 of the drawings, a representative operational embodiment may take the form of a solar operated pump 10 for desalination by reverse osmosis or to pump water to a solar distillation unit or to a solar heater, etc. The solar powered pump has an elongate cylinder 15 closed at opposite ends by a pair of caps 16 and 17. At least one clear window portion 18 is provided which is transparent to predetermined wavelengths of light or other suitable incident electromagnetic radiation. A piston 20, appropriately sized and sealed about its periphery, is fitted within cylinder 15 to permit axial, bidirectional longitudinal travel therein and to define a pair of internal chambers 15a and 15b. Optionally, the piston could be a flexible wall secured about its periphery to the inside of cylinder 15 and having a sufficient resiliency for a responsive flexure to effect the pumping action to be described.

A pair of one-way valves 25 and 26 are provided on elongate cylinder 15 to assure the selective flow of a fluid, such as seawater for example, from an inlet duct 27 into internal chamber 15a and from internal chamber 15a to an outlet duct 28. A displacement of piston 20 to the right, for example, causes check valve 25 to close and check valve 26 to open to draw seawater from inlet duct 27 into chamber 15a. Displacement of piston 20 to the left closes check valve 26 and opens check valve 25 to force at least part of the seawater in chamber 15a through outlet duct 28. Typically, this pumping device may be used to feed seawater to a reverse osmosis unit, a solar heater or a wide variety of fluid utilization systems.

On the right side of piston 20 internal chamber 15b is filled with an appropriate pH dependent dye 60, having an appropriate acid dissociation constant (pKa). A secondary cylinder 35 is located near elongate cylinder 15 and is hydraulically coupled to internal chamber 15b via a feeder duct 36. The feeder duct permits the exchange of the pH dependent dye to and from internal chamber 15b and secondary cylinder 35 through a passageway 36' that penetrates the wall of the elongate cylinder. A slave piston 37, appropriately sized and sealed about its periphery, is fitted within secondary cylinder 35 to permit axial, bidirectional longitudinal displacement therein. The axial, bidirectional longitudinal displacement of the slave piston is in response to ducted volumes of the pH dependent dye which pass through feeder duct 36 from internal chamber 15b as piston 20 is reciprocally displaced.

An elongate push rod 38 from slave piston 37 is pinned 39' to slotted lever 39. The lever also is rotatably coupled via pin 39" to a disc 40 journaled in an appropriate support 41 that may be mounted on elongate cylinder 15. Longitudinal 18 displacement of the push rod effects a rotation of disc and a suitable beveled gear arrangement 45 translates the rotational motion of disc 40 into an orthogonally oriented rotary displacement of an interconnected plate or disc-shaped bracket 46. Slotted lever 39 is depicted in FIG. 2 to provide for a lost motion of the push rod so that a delayed rotation of the associated structure, will occur. This allows the push rod to turn the beveled gear arrangement and its associated disc-shaped bracket 46 principally at the top and the bottom of a stroke. Also, the push rod may have a cam-shape to impart a selective non-uniform or exponential displacement of the disk-shaped bracket. Such a displacement may be preferred to change the positioning of the filters to create a more gradual or to a more abrupt transition of the select wavelengths. Optionally, the disc is a gear directly coupled to a rack on the push rod via mating teeth to displace the bracket rotationally uniformly as the piston moves.

Bracket 46 is configured to provide at least a pair of appropriately shaped windows 46a which may be a semicircular wedge-shape to provide a support for optical filters 50 and 51. The optical filters may be suitably colored plastic or glass, to assure that the electromagnetic radiation emitted from a source 55, such as the sun, is filtered to transmit at least the discrete wavelengths of electromagnetic radiation necessary to effect the desired pH changes in pH dependent dye solution 60 that fills internal chamber 15b. In the case of the Bromocresol Green pH dependent dye solution referred to above, optical filters 50 and 51 are a yellow filter and a blue filter, respectively, to cause the desired pH changes. The pH dependent dye solution fills the volume beneath window 18 to receive the appropriate electromagnetic radiation.

Polyelectrolyte fibers or gel 65, such as polyvinyl alcohol-poly-acrylic acid (PVA-PAA), are immersed in pH dependent dye solution 60 to receive electromagnetic radiation through clear window 18 and are appropriately disposed or appropriately coupled by bonding or tying to transfer force to piston 20 and cap 15. The fibers may be simply tied with suitable knots to appropriate appendages provided on the piston and the wall, although other suitable means of affixing the fibers will be apparent to one skilled in the art to which this invention pertains. The electromagnetic radiation source may be the sun, although any other suitable light sources or electromagnetic radiation sources can be provided as appropriate in a given pH dependent dye solution or situation. The selective radiations from a host of laser sources can be drawn upon for appropriate actuation and powering of this inventive concept if a designer so elects. For example, a particular application may call for a more directed and/or selective actuation of fibers and gel such as by using appropriately disposed optical fibers to channel the radiation to more completely derive the benefits of this inventive concept. In either case when electromagnetic radiation from the source impinges on the filters, other light may be absorbed and a predetermined light passes through. In this example, the yellow filter and the blue filter in window 50 and 51 transform impinging sunlight into either yellow or blue light.

When yellow filter 50 is interposed between source 55 and window 18, yellow light impinges on a pH dependent dye solution 60 and fiber 65 and the fiber appropriately contracts. This causes a displacement to the left of piston 20 and a drawing-in of seawater to chamber 15a. The pH dependent dye solution 60 is forced from chamber 15b and into secondary cylinder 35 via feeder duct 36 so that slave piston 37 pushes push rod 38 upward, away from cylinder 15. The upward motion of push rod 38 translates a force to disc 40 that rotates interconnected beveled gear arrangement 45. Beveled gear arrangement 45 responsively rotates bracket 46 which interposes blue filter 51 between light source 55 and window 18.

Blue light passing through blue filter 51 impinges on pH dependent dye solution 60 to change its pH. This change in pH effects polyelectrolyte gel or fiber 65 to at least relax it to its original dimension. The change in pH could also effect an expansion or extension of fiber 65 and a consequent displacement of piston 20 to the left. The displacement closes check valve 26, opens check valve 25 and pumps seawater from chamber 15a to outlet duct 28 and to the reverse osmosis unit.

The leftward displacement of piston 20 also draws-in pH-dependent dye solution 60 from secondary cylinder 35 to chamber 15b via duct 36. Slave piston 37 and push rod 38 are displaced downwardly, oppositely rotating disc 40. This opposite rotation of disc 40 causes bevel gear arrangement 45 to rotate bracket 46 appropriately and realign the yellow filter between light source 55 and clear window 18. Yellow light on the polyelectrolyte gel or fiber 60 causes a repeat of the cycle.

Optionally, a tensile or compressive force spring 30 may be included to aid in a displacement of piston 20 one way or the other. Different polyelectrolyte gels or fibers may prove to be more efficient or workable when a suitable spring is utilized to displace piston 20.

A different configuration in accordance with this inventive concept provides an additional polyelectrolyte gel or fiber which is immersed in a pH-dependent dye solution in internal chamber 15a and is connected between cap 16 and piston 20. A clear window portion would also be included on this other side of the piston 20 to pass the appropriate wavelengths of actuating electromagnetic radiation. When the electromagnetic radiations pass through the aligned filters, the polyelectrolyte gel or fiber on both sides of piston would expand and contract responsibly in an alternate fashion to additively transfer their tensile and pushing forces to piston 20. The piston could be connected to a push rod, not shown, that extends through cap 16 to displace a slidably sealed follower-piston that functions as a mover in a pump which operates in much the same manner as outlined above.

Looking to FIG. 3, another embodiment of this inventive concept is as a fiber optic-controlled manipulator or claw 70 provided with a number of pinned articulated segments 71, 72, 73, 74, 75 and 76. Separate ones or discrete groups of fiber optic cables 77a, 77b, 77c, 77d and 77e are interwoven or otherwise disposed within a polymeric gel (the "muscle") contained in and secured at opposite ends to opposite parts of an inner wall of individual flexible sacs or pods 78a, 78b, 78c, 78d and 78e which are filled with an appropriate pH dependent dye solution. The pods are connected to adjacent pinned segments of the claw on the outside wall of individual flexible sacs or pods at a location at or near the opposite parts by suitable means, such as an adhesive.

The necessary light radiation or other suitable electromagnetic radiation is provided by an appropriate source 80, such as lasers for example. The source emits the light or radiations of various wavelengths and intensities to the optical fibers as needed to affect the pH of the pH dependent dye solution. The optical fibers may have a configuration and, perhaps, changed surface properties to bend the radiations away from the core of the fiber at each pod to thereby direct and dissipate the radiations throughout each pod to substantially, uniformly effect the pH changes in the solution.

A computer 90 or other suitable controller is suitably programmed by one skilled in the art to provide a desired switching sequence. This switching sequence selectably couples the radiations from source 80 to different ones of the optical fiber cables which transmit the radiations to discrete flexible pods. The selective coupling of the radiations to the pods gives a really fine muscular control and actuation of the claw.

Looking to FIG. 4, this fine muscular control is attributed to the fact that the appropriate radiations transmitted to each pod by optical fibers or fiber optic cables 77' affect the pH dependent dye 60'. This causes the immersed polyelectrolyte fibers (or gel) 65' secured at opposite ends to the inner wall of a pod 68' to expand as shown by expanded pod 78' or contract as shown by a contracted pod 78" in FIG. 5. The internal volume of each pod stays, essentially, the same. Optionally, a feedback mechanism is associated with the computer by which the computer knows or provides an indication of exactly how much to change the energy and wavelengths of the radiations going through each optical fiber. This mechanism may be based on muscle force or size of the muscle, etc. using appropriate sensors 95, 95', (piezoelectric), attached to the pods or otherwise suitably located on the articulated segments. In addition, a visual observation could be relied upon to allow a manual command of the computer or light source for control purposes. Actuators of both great strength and tactile sensitivity are within the capabilities of this inventive concept to fabricate working robots or prosthetic devices.

Having the aforedescribed examples in mind, a host of other manipulator and actuator applications will readily suggest themselves to one skilled in the art using the disclosed radiation powered fibers (gels) in the appropriate pH dependent dyes with beamed or optical fiber passed radiation. Therefore, the illustrative examples provided herein are not intended to be taken as limiting of this inventive concept.

A variety of polyelectrolyte fibers, or when hydrated, polyelectrolyte gels may be chosen by one skilled in the art for selective light actuation and powering in accordance with this inventive concept. For example, this inventive concept can utilize all polyelectrolyte gels which respond to pH changes by significantly changing their volume. However, the greater the optical transmittance of the gel, the more likely that the incident radiant energy will be transmitted to changes of pH rather than heat. Typical polyelectrolyte fibers, or when hydrated, polyelectrolyte gels may be made from poly methacrylic acid, polymerized isopropylacrylamide, polyvinyl alcohol-polyacrylic acid (PVA-PAA), polyvinyl alcohol-polyacrylic acid-polyallylamine or protein polyelectrolytes (ex. collagen). U.S. Pat. No. 4,732,930 entitled "Reversible Discontinuous Volume Changes of Ionized Isopropylacrylamide Cells" by Toyoichi Tanaka et al. also identifies suitable gels. These typical polyelectrolyte fiber substances, (or gels), listed herein are for the purpose of demonstration only and are not to be construed as limiting.

A number of pH dependent dyes may be chosen by one skilled in the art for selective light actuation and powering in accordance with this inventive concept. For example, this inventive concept can utilize dyes in solution which change pH for all portions of the practical pH range (1–13). The best dye is the one with an acid dissociation constant (pKa) which coincides with the null point of the polyelectrolyte fiber. The following pH indicators may be selected by one skilled in the art for appropriate pH dependent dye solutions in accordance with this inventive concept.

| Name | pH Range | pKa | Wavelength (nm) |
| --- | --- | --- | --- |
| Thymolsulfonphthalein | 1.2–2.8 | 1.65 | 544–430 |
| Tetrabromophenol-sulfonphthalein (Bromocresol Green) | 3.0–4.6 | 4.10 | 436–592 |
| Dimethylaminoazobenzene-p-sulfonate | 3.1–4.4 | 3.46 | 522–464 |
| Tetrabromo-m-cresol-sulfonphthalein | 3.8–5.4 | 4.90 | 444–617 |
| Dimethylaminoazobenzene-o-carboxylic acid | 4.2–6.3 | 5.00 | 444–617 |
| Dibromo-o-cresol-sulfonphthalein | 5.2–6.8 | 6.40 | 433–591 |
| Dibromothymolsulfophthalein | 6.2–7.6 | 7.30 | 433–617 |
| Phenolsulfonphthalein | 6.8–8.4 | 8.00 | 433–558 |
| o-Cresolsulfonphthalein | 7.2–8.8 | | 434–572 |
| Thymolsulfonphthalein | 8.0–9.6 | 9.20 | 430–596 |
| Di-p-dioxydiphenylphthalide | 8.3–10.0 | | 553 |

These typical substances for the pH dependent dye solutions listed above are for the purpose of demonstration only and are not to be construed as limiting.

A main advantage of this technique is that the actuating and powering electromagnetic radiation, such as light, changes the pH of the solution immediately and reversibly around the fiber. This causes every segment of the fiber to contract at substantially the same time. The need to add acid or base solutions is avoided and there are no delays due to the diffusion of hydrogen or hydroxide ion to the individual fiber sites. As an alternative to this inventive concept, an acid or base solution otherwise would have to be added to the fiber which is very slow and cumbersome.

Obviously, many modifications and variations of the present invention are possible in the light of the above teachings. It is therefore to be understood that within the scope of the appended claims, the invention may be practiced otherwise than as specifically described.

I claim:

1. A visible light actuated apparatus comprising:
    a source of visible light having the capability of selectively emitting either of at least one first wavelength of visible light or at least one second wavelength of visible light, said at least one first wavelength of visible light and said at least one second wavelength of visible light being emitted within the spectrum of visible light of between 400 nm to 700 nm and at an amplitude sufficient to effect a pH change;
    a pH dependent dye solution, disposed to receive said at least one first wavelength of visible light or said at least one second wavelength of visible light, having the property of being responsive to said at least one first wavelength of visible light or said at least one second wavelength of visible light to change its pH to either of two discrete pH values within a pH range of 3 to 11, respectively; and
    a polyelectrolyte fiber, disposed in said pH dependent dye solution, having the property to change its volume in response to one of said two discrete pH values of said pH dependent dye solution to produce a selective first physical displacement and to reversibly change its volume in response to the other of said two discrete pH values of said pH dependent dye solution to produce a selective reversible second physical displacement.

2. An apparatus according to claim 1 in which said pH dependent dye solution has an acid dissociation constant pKa within plus or minus 1 pH unit of the pH null point of said polyelectrolyte fiber.

3. An apparatus according to claim 2 in which said at least one first wavelength of visible light and said at least one second wavelength of visible light emitted by said source of visible light are predetermined to change said two discrete pH values of said pH dependent dye solution to be greater than and less than said pH null point of said polyelectrolyte fiber, respectively.

4. An apparatus according to claim 1 in which said pH polyelectrolyte fiber is polyvinyl alcohol-polyacrylic acid (PVA-PAA).

5. An apparatus according to claim 1 in which said polyelectrolyte fiber is polyvinyl alcohol-polyacrylic acid-polyallylamine.

6. An apparatus according to claim 1 in which said polyelectrolyte fiber is protein polyelectrolytes.

7. An apparatus according to claim 3 in which said polyelectrolyte fiber is poly methacrylic acid.

8. An apparatus according to claim 3 in which said pH polyelectrolyte fiber is polyvinyl alcohol-polyacrylic acid (PVA-PAA).

9. An apparatus according to claim 3 in which said polyelectrolyte fiber is polyvinyl alcohol-polyacrylic acid-polyallylamine.

10. An apparatus according to claim 3 in which said polyelectrolyte fiber is protein polyelectrolytes.

11. A method actuated by visible light comprising:
    radiating at least one first wavelength of visible light or at least one second wavelength of visible light from a source of at least one first wavelength of visible light and at least one second wavelength of visible light, said at least one first wavelength of visible light and said at least one second wavelength of visible light being emitted within the spectrum of visible light of between 400 nm to 700 nm and at an amplitude sufficient to effect a pH change;
    providing a pH dependent dye solution, disposed to receive said at least one first wavelength of visible light or said at least one second wavelength of visible light, having the property of being responsive to said at least one first wavelength or said at least one second wavelength of visible light to change its pH within a pH range of 3 to 11;
    immersing a polyelectrolyte fiber in said pH dependent dye solution, said polyelectrolyte fiber having the property to change its volume in response to one of said two discrete pH values of said pH dependent dye solution to produce a selective first physical displacement and to reversibly change its volume in response to the other of said two discrete pH values of said pH dependent dye solution to produce a selective reversible second physical displacement;
    directly radiating said at least one first wavelength of visible light or said at least one second wavelength of visible light from said source of said at least one first wavelength of visible light and said at least one second wavelength of visible light to impinge on said pH dependent dye solution;
    changing the pH in said pH dependent dye solution to one of said two discrete pH values by said directly radiating; changing the volume of said polyelectrolyte fiber in response to said one of said two discrete pH values to produce a selective first physical displacement;
    changing the pH in said pH dependent dye solution to the other of said two discrete pH values by said directly radiating; and
    reversibly changing the volume of said polyelectrolyte fiber in response to the other of said two discrete pH values of said pH dependent dye solution to produce a selective reversible second physical displacement.

12. A method according to claim 11 in which the providing of said pH dependent dye solution is the selecting of said pH dependent dye solution to have an acid dissociation constant pKa within plus or minus 1 pH unit of the pH null point of said polyelectrolyte fiber.

13. A method according to claim 12 in which said at least one first wavelength of visible light and said at least one second wavelength of visible light radiated by said source of visible light are predetermined to change said two discrete pH values of said pH dependent dye solution to be greater than and less than said pH null point of said polyelectrolyte fiber, respectively.

14. A method according to claim 11 in which said pH polyelectrolyte fiber is polyvinyl alcohol-polyacrylic acid (PVA-PAA).

15. A method according to claim 11 in which said polyelectrolyte fiber is polyvinyl alcohol-polyacrylic acid-polyallylamine.

16. A method according to claim 11 in which said polyelectrolyte fiber is protein polyelectrolytes.

17. A method according to claim 13 in which said polyelectrolyte fiber is poly methacrylic acid.

18. A method according to claim 13 in which said pH polyelectrolyte fiber is polyvinyl alcohol-polyacrylic acid (PVA-PAA).

19. A method according to claim 13 in which said polyelectrolyte fiber is polyvinyl alcohol-polyacrylic acid-polyallylamine.

20. A method according to claim 13 in which said polyelectrolyte fiber is protein polyelectrolytes.

21. An apparatus for pumping a fluid in response to visible light comprising:

a source of visible light having the capability of selectively emitting either of at least one first wavelength of visible light or at least one second wavelength of visible light, said at least one first wavelength of visible light and said at least one second wavelength of visible light being emitted within the spectrum of visible light of between 400 nm to 700 nm and at an amplitude sufficient to effect a pH change;

means for defining a first chamber and a second chamber having a displaceable wall in communication with at least one of the chambers, the defining means being provided with a portion transparent to said at least one first wavelength of visible light and at least one said second wavelength of visible light and being further provided with at least one check valve arranged in communication with said second chamber to assure a pumping of said fluid in response to said selective displacement of said displaceable wall;

a pH dependent dye solution, disposed in said first chamber to receive said at least one first wavelength of visible light or at least one said second wavelength of visible light, having the property of being responsive to said at least one first wavelength of visible light or said at least one second wavelength of visible light to change its pH to either of two discrete pH values within a pH range of 3 to 11, respectively; and a polyelectrolyte fiber, disposed in said pH dependent dye solution and coupled to said displaceable wall, said polyelectrolyte fiber having the property to change its volume in response to one of said two discrete pH values of said pH dependent dye solution to produce a selective first physical displacement of said wall and to reversibly change its volume in response to the other of said two discrete pH values of said pH dependent dye solution to produce a selective reversible second physical displacement of said wall.

22. An apparatus according to claim 21 in which said pH dependent dye solution has an acid dissociation constant pKa within plus or minus 1 pH unit of the pH null point of said polyelectrolyte fiber.

23. An apparatus according to claim 1 in which said source of visible light having the capability of selectively emitting either of at least one first wavelength of visible light or at least one second wavelength of visible light includes at least one optical fiber oriented to direct said at least one first wavelength or said at least one second wavelength of visible light on said pH dependent dye solution to effect a change in the pH in said pH dependent dye solution and a consequent change in volume in said polyelectrolyte fiber.

24. An apparatus according to claim 23 further including:

a flexible pod containing said pH dependent dye solution and said polyelectrolyte fiber, said polyelectrolyte fiber, being attached at opposite ends thereof to an inner wall of said pod and said optical fiber optically communicating with said pH dependent dye solution in said pod.

25. An apparatus according to claim 24 further including:

at least two segments joined together by a pin to permit relative rotational motion therebetween and having at least one said pod connected to said two segments to impart said relative rotational motion therebetween.

26. A method according to claim 11 further including:

providing at least one optical fiber to transmit said at least one first wavelength of visible light or said at least one second wavelength of visible light from said source of said at least one first wavelength of visible light and said at least one second wavelength of visible light to assure said radiating.

27. A method according to claim 26 further including:

providing a pod to contain said pH dependent dye solution and said polyelectrolyte fiber, said polyelectrolyte fiber, being attached at opposite ends thereof to an inner wall of said pod and said optical fiber optically communicating with said pH dependent dye solution in said pod.

28. An apparatus according to claim 22 in which said at least one first wavelength of visible light and said at least one second wavelength of visible light emitted by said source of visible light are predetermined to change said two discrete pH values of said pH dependent dye solution to be greater than and less than said pH null point of said polyelectrolyte fiber or gel, respectively.

29. An apparatus according to claim 1 in which said polyelectrolyte fiber is poly methacrylic acid.

30. A method according to claim 11 in which said polyelectrolyte fiber is poly methacrylic acid.

31. An apparatus according to claim 28 in which said source of visible light having the capability of selectively emitting either of at least one first wavelength of visible light or at least one second wavelength of visible light includes at least one optical fiber oriented to direct said at least one first wavelength of visible light or said at least one second wavelength of visible light on said pH dependent dye solution to effect a change in the pH in said pH dependent dye solution and a consequent change in volume in said polyelectrolyte fiber.

32. An apparatus according to claim 31 further including:

a flexible pod containing said pH dependent dye solution and said polyelectrolyte fiber, said polyelectrolyte fiber, being attached at opposite ends thereof to an inner wall of said pod and said optical fiber optically communicating with said pH dependent dye solution in said pod.

33. A method according to claim 13 further including:

providing at least one optical fiber to transmit said at least one first wavelength of visible light or at least one said second wavelength of visible light from said source of said at least one first wavelength of visible light and said at least one second select wavelength of visible light to assure said radiating.

34. A method according to claim 33 further including:

providing a pod to contain said pH dependent dye solution and said polyelectrolyte fiber, said polyelectrolyte fiber, being attached at opposite ends thereof to an inner wall of said pod and said optical fiber optically communicating with said pH dependent dye solution in said pod.

35. A visible light actuated apparatus comprising:

a source of visible light having the capability of selectively emitting either of at least one first wavelength of visible light or at least one second wavelength of visible light, said at least one first wavelength of visible light and said at least one second wavelength of visible light being emitted within the spectrum of visible light of between 400 nm to 700 nm and at an amplitude sufficient to effect a pH change;

a pH dependent dye solution, disposed to receive said at least one first wavelength of visible light or said at least one second wavelength of visible light, having the property of being responsive to said at least one first wavelength of visible light or said at least one second wavelength of visible light to change its pH to either of two discrete pH values within a pH range of 3 to 11, respectively; and a polyelectrolyte gel, disposed in said pH dependent dye solution, having the property to change its volume in response to one of said two discrete pH values of said pH dependent dye solution to produce a selective first physical displacement and to reversibly change its volume in response to the other of said two discrete pH values of said pH dependent dye solution to produce a selective reversible second physical displacement.

36. An apparatus according to claim 35 in which said pH dependent dye solution has an acid dissociation constant pKa within plus or minus 1 pH unit of the pH null point of said polyelectrolyte gel.

37. An apparatus according to claim 35 in which said at least one first wavelength of visible light and said at least one second wavelength of visible light radiated by said source of visible light are predetermined to change said two discrete pH values of said pH dependent dye solution to be greater than and less than said pH null point of said polyelectrolyte gel, respectively.

38. An apparatus according to claim 35 in which said polyelectrolyte gel is polymerized isopropylacrylamide.

39. An apparatus according to claim 36 in which said polyelectrolyte gel is poly methacrylic acid.

40. An apparatus according to claim 36 in which said polyelectrolyte gel is polymerized isopropylacrylamide.

41. A method actuated by visible light comprising:
radiating at least one first wavelength of visible light or at least one second wavelength of visible light from a source of at least one first wavelength of visible light and at least one second wavelength of visible light, said at least one first wavelength of visible light and said at least one second wavelength of visible light being emitted within the spectrum of visible light of between 400 nm to 700 nm and at an amplitude sufficient to effect a pH change;

providing a pH dependent dye solution, disposed to receive said at least one first wavelength of visible light or said at least one second wavelength of visible light, having the property of being responsive to said at least one first wavelength or said at least one second wavelength of visible light to change its pH within a pH range of 3 to 11;

immersing a polyelectrolyte gel in said pH dependent dye solution, said polyelectrolyte gel having the property to change its volume in response to one of said two discrete pH values of said pH dependent dye solution to produce a selective first physical displacement and to reversibly change its volume in response to the other of said two discrete pH values of said pH dependent dye solution to produce a selective reversible second physical displacement;

directly radiating said at least one first wavelength of visible light or said at least one second wavelength of visible light from said source of said at least one first wavelength of visible light and said at least one second wavelength of visible light to impinge on said pH dependent dye solution;

changing the pH in said pH dependent dye solution to, one of said two discrete pH values by said directly radiating; changing the volume of said polyelectrolyte gel in response to said one of said two discrete pH values to produce a selective first physical displacement;

changing the pH in said pH dependent dye solution to the other of said two discrete pH values by said directly radiating; and reversibly changing the volume of said polyelectrolyte gel in response to the other of said two discrete pH values of said pH dependent dye solution to produce a selective reversible second physical displacement.

42. A method according to claim 41 in which the providing of said pH dependent dye solution is the selecting of said pH dependent dye solution to have an acid dissociation constant pKa within plus or minus 1 pH unit of the pH null point of said polyelectrolyte gel.

43. A method according to claim 42 in which said at least one first wavelength of visible light and said at least one second wavelength of visible light radiated by said source of visible light are predetermined to change said two discrete pH values of said pH dependent dye solution to be greater than and less than said pH null point of said polyelectrolyte gel, respectively.

44. A method according to claim 41 in which said polyelectrolyte gel is polymerized isopropylacrylamide.

45. A method according to claim 43 in which said polyelectrolyte gel is poly methacrylic acid.

46. A method according to claim 43 in which said polyelectrolyte gel is polymerized isopropylacrylamide.

47. An apparatus for pumping a fluid in response to visible light comprising:
a source of visible light having the capability of selectively emitting either of at least one first wavelength of visible light or at least one second wavelength of visible light, said at least one first wavelength of visible light and said at least one second wavelength of visible light being emitted within the spectrum of visible light of between 400 nm to 700 nm and at an amplitude sufficient to effect a pH change;

means for defining a first chamber and a second chamber having a displaceable wall in communication with at least one of the chambers, the defining means being provided with a portion transparent to said at least one first wavelength of visible light and at least one said second wavelength of visible light and being further provided with at least one check valve arranged in communication with said second chamber to assure a pumping of said fluid in response to said selective displacement of said displaceable wall;

a pH dependent dye solution, disposed in said first chamber to receive said at least one first wavelength of visible light or at least one said second wavelength of visible light, having the property of being responsive to said at least one first wavelength of visible light or said at least one second wavelength of visible light to change its pH to either of two discrete pH values within a pH range of 3 to 11, respectively; and a polyelectrolyte gel, disposed in said pH dependent dye solution and coupled to said displaceable wall, said polyelectrolyte gel having the property to change its volume in response to one of said two discrete pH values of said pH dependent dye solution to produce a selective first physical displacement of said wall and to reversibly change its volume in response to the other of said two discrete pH values of said pH dependent dye solution to produce a selective reversible second physical displacement of said wall.

48. An apparatus according to claim 47 in which said pH dependent dye solution has an acid dissociation constant pKa within plus or minus 1 pH unit of the pH null point of said polyelectrolyte gel.

49. An apparatus according to claim 35 in which the at least one discrete wavelength of electromagnetic radiation source includes at least one optical fiber oriented to direct said at least one discrete wavelength of electromagnetic radiation to impinge on said pH dependent dye solution to effect a change in the pH in said pH dependent dye solution and a consequent change in volume in said polyelectrolyte gel and thereby power said selective displacement.

50. An apparatus according to claim 49 further including:

a flexible pod containing said pH dependent dye solution and said polyelectrolyte gel, said polyelectrolyte gel, being attached at opposite ends thereof to an inner wall of said pod and said optical fiber optically communicating with said pH dependent dye solution in said pod.

51. An apparatus according to claim 50 further including:

at least two segments joined together by a pin to permit relative rotational motion therebetween and having at least one said pod connected to said two segments to impart said relative rotational motion therebetween.

52. A method according to claim 41 further including:

providing at least one optical fiber to transmit said at least one discrete wavelength of electromagnetic radiation from a source of said at least one discrete wavelength of electromagnetic radiation to assure said radiating.

53. A method according to claim 52 further including:

providing a pod to contain said pH dependent dye solution and said polyelectrolyte gel, said polyelectrolyte gel, being attached at opposite ends thereof to an inner wall of said pod and said optical fiber optically communicating with said pH dependent dye solution in said pod.

54. An apparatus according to claim 47 in which the at least one discrete wavelength of electromagnetic radiation source includes at least one optical fiber oriented to direct said at least one discrete wavelength of electromagnetic radiation through to impinge on said pH dependent dye solution to effect a change in the pH in said pH dependent dye solution and a consequent change in volume in said polyelectrolyte gel and thereby power said selective displacement of said moveable wall to assure said pumping of said fluid.

55. An apparatus according to claim 35 in which said polyelectrolyte gel is poly methacrylic acid.

56. A method according to claim 41 in which said polyelectrolyte gel is poly methacrylic acid.

57. An apparatus according to claim 43 in which said source of visible light having the capability of selectively emitting either of at least one first wavelength of visible light or at least one second wavelength of visible light includes at least one optical fiber oriented to direct said at least one first wavelength of visible light or said at least one second wavelength of visible light on said pH dependent dye solution to effect a change in the pH in said pH dependent dye solution and a consequent change in volume in said polyelectrolyte gel.

58. An apparatus according to claim 57 further including:

a flexible pod containing said pH dependent dye solution and said polyelectrolyte gel, said polyelectrolyte gel, being attached at opposite ends thereof to an inner wall of said pod and said optical fiber optically communicating with said pH dependent dye solution in said pod.

59. A method according to claim 41 further including:

providing at least one optical fiber to transmit said at least one first wavelength of visible light or at least one said second wavelength of visible light from said source of said at least one first wavelength of visible light and said at least one second select wavelength of visible light to assure said radiating.

60. A method according to claim 43 further including:

providing a pod to contain said pH dependent dye solution and said polyelectrolyte gel, said polyelectrolyte gel, being attached at opposite ends thereof to an inner wall of said pod and said optical fiber optically communicating with said pH dependent dye solution in said pod.

* * * * *